United States Patent [19]

Meybeck et al.

[11] Patent Number: 5,374,452
[45] Date of Patent: Dec. 20, 1994

[54] PROCESS FOR PRODUCING ORGANIZED POWDERS BY SPRAYING FROM AT LEAST TWO SETS OF PARTICLES, AND ORGANIZED POWDERS THUS OBTAINED

[76] Inventors: Alain Meybeck, Les Poissons-20ter rue de Bezons, 92400 Courbevoie; Philippe Antoine, 8 quai du Gén/e,acu/e/ ral de Gaulle, 53200 Chateau Gontier, both of France

[21] Appl. No.: 6,204

[22] Filed: Jan. 19, 1993

Related U.S. Application Data

[63] Continuation of Ser. No. 743,285, filed as PCT/FR90/00588, Aug. 3, 1990, abandoned.

[51] Int. Cl.$^5$ ............................................... B05D 7/00
[52] U.S. Cl. .................................. 427/212; 427/215; 427/218; 427/222
[58] Field of Search ............... 427/222, 212, 215, 218

[56] References Cited

U.S. PATENT DOCUMENTS

| | | | |
|---|---|---|---|
| 4,016,099 | 4/1977 | Wellman et al. | 427/222 |
| 4,209,550 | 6/1980 | Hagenbach et al. | 427/221 |
| 4,233,387 | 11/1980 | Mammino et al. | 427/221 |
| 4,438,179 | 3/1984 | Solc | 427/214 |
| 4,477,492 | 10/1984 | Bergna et al. | 427/215 |
| 4,593,007 | 6/1986 | Novinski | 428/403 |
| 4,908,391 | 3/1990 | Melber et al. | 427/222 |
| 5,017,383 | 5/1991 | Ozawa et al. | 427/212 |
| 5,041,334 | 8/1991 | Nakajima et al. | 427/407 |

*Primary Examiner*—Shrive Beck
*Assistant Examiner*—Brian K. Talbot
*Attorney, Agent, or Firm*—Rosen, Dainow & Jacobs

[57] ABSTRACT

The invention relates to a process for producing organized powders. The powder comprises a set of core particles and a set of satellite particles. To form the organized powders, a substantially homogenous dispersion of each set is made in a dispersing liquid; the resultant dispersion is then sprayed in suitable conditions to form the organized powder. The organized powders obtained are characterized by a very uniform covering of the core particles regardless of their shape.

19 Claims, No Drawings

PROCESS FOR PRODUCING ORGANIZED POWDERS BY SPRAYING FROM AT LEAST TWO SETS OF PARTICLES, AND ORGANIZED POWDERS THUS OBTAINED

This application is a continuation of application Ser. No. 07/743,285, filed as PCT/FR90/00588, on Aug. 3, 1990, now abandoned.

The present invention relates essentially to a process for producing organized powders from different-sized particles belonging to at least two populations of particles of substantially homogeneous size. It also relates to the organized powders thus obtained.

In the present document, the expression "organized powder" designates the regular assembly of particles of different sizes, particles of small sizes, or "satellite particles", which settle in regular order on the surface of a particle of larger size, or "parent" or "core particle", so as to cover up the latter in one or more layers, either partly or completely.

In the prior art, various processes are known for producing organized powders obtained from particles of different sizes. For example, document JP-A-62-083 029 NARA describes a process and a device permitting the preparation of organized powders from two sets of particles of homogeneous sizes by a technique known as percussion impact. In general, the core particles have a mean diameter of about 0.1 $\mu$m to 100 $\mu$m and the satellite particles a mean diameter of about 0.01 $\mu$m to 10 $\mu$m. With this process, a good adhesion of the satellite particles to the core particles is obtained, with a substantially uniform covering, the whole constituting a system generally called "hybrid powder".

In addition, various articles have been published in the literature concerning organized mixtures. In particular, reference can be made to the revue, Powder Technology 11 (1975) 41–44 or 25 (1980) 115–119.

However, the techniques used priorly are not very satisfactory. In particular, they are complex and costly, hence difficult to use on an industrial scale.

It is therefore the object of the present invention to solve the new technical problem consisting in providing a process for producing organized powders in a simple way, permitting the production of organized powder in reproducible manner, the parameters of which process can be adapted to industrial demand and at a low cost.

This new technical problem is solved for the first time in an extremely simple way by the present invention, which makes it suitable for use on an industrial scale.

Thus, in a first aspect, the present invention provides a process for producing organized powders from particles of different sizes belonging to at least two sets of particles of substantially homogeneous sizes, comprising respectively, at least one set of core particles and at least one set of satellite particles of smaller size than that of the core particles, characterized in that in a first step, a substantially homogeneous dispersion of each set is made in a dispersing liquid; and, in a second step, said dispersion is sprayed in suitable conditions to allow the formation of said organized powder.

In the present description and claims, the term "spraying" should be understood to have a broad meaning, said term notably covering the terms "nebulization" and "atomization".

According to a particular embodiment, the spraying of said dispersion is performed inside an enclosure in conditions of pressure and temperature such as to allow the evaporation of the dispersing liquid, thus leading to the formation of said organized powder.

Advantageously, the spraying is performed in a gaseous fluid brought to a sufficient temperature to cause the evaporation of the dispersing liquid.

The temperature of the gaseous fluid is preferably higher than the boiling point of the dispersing liquid.

In particular, the gaseous fluid is constituted by air.

It will be noted that, obviously, when carrying out the present invention, the dispersing liquid should not be liable to dissolve said particles.

According to a particular variant of embodiment of the process according to the invention, said dispersion is produced in one liquid only.

Advantageously, the dispersing liquid is constituted by water or an aqueous solution.

According to another particular variant of embodiment, the dispersion of each set is made in one particular dispersing liquid and the two dispersions are thereafter mixed homogeneously either before spraying or at spraying time.

According to another variant of embodiment, a wetting substance, such as a surfactant, for example like the product sold under the denomination TWEEN 20 which is sorbitan monolaurate polyoxyalkylene, is added to the dispersing liquid prior to the introduction of the particles, in a concentration of 1% by weight of dry material, i.e. of the total quantity of particles to be dispersed.

In general, the dry material content of the dispersing liquid, i.e. the ratio of the quantity by weight of core particles and of satellite particles to the quantity by weight of dispersing liquid, can range between 5 and 40%, preferably between 10 and 20%, and preferably still between 10 and 15%.

According to a particular characteristic, the mean diameter of the satellite particles is advantageously less than or equal to about one fifth of the mean diameter of the core particles.

According to another characteristic, the relative proportion by weight of the satellite particles relative to the core particles, may vary within wide limits, and is dependent on the structure wanted for the organized powder.

More precisely, the relative proportion by weight (R) of the satellite particles relative to the core particles will be determined as a function of the number of satellite particles which are expected to adhere to one core particle and of the mean masses of the satellite particles and of the core particles, according to the formula:

$$R = \frac{nM}{M_o}$$

in which n is the mean number of satellite particles adhering to one core particle, M is the mean mass of a satellite particle and $M_o$ is the mean mass of a core particle.

The number of satellite particles adhering to a core particle is essentially dependent on the surface occupied by each satellite particle on a core particle, of the surface occupied on the core particle (covering of the core particle may be partial or total) and of the number of layers of satellite particles on a core particle (unilayered or multilayered structure).

In the case of a unilayered structure, and for a total covering of the core particles, the theoretical number of satellite particles liable to adhere to one core particle is equal to the ratio of the total surface of a core particle to the surface occupied by a satellite particle.

This ratio therefore permits a calculation of the theoretical proportion by weight of each one of the two sets of particles, in percentage with respect to the total weight of powder.

For implementing the present invention, the proportions by weight will thus be selected so as to be close to the theoretical values. However, and in particular to allow for a certain variability in the shape of the particles, it will be possible to deviate more or less from said theoretical value in order to obtain the target results.

By way of examples, Table I sums up the theoretical calculation of the relative proportion by weight (or by mass) of the satellite particles relatively to the core particles in the two most common cases, where the satellite particles are substantially spherical-shaped and the core particles are substantially spherical-shaped or cylindrical-shaped such as a disk.

In both cases, the surface of core particle occupied by a satellite particle has been considered to be substantially equal to the projected surface of said satellite particle, meaning in effect its equatorial surface.

In the case where the core particles are disk-shaped, the height h of the disk is considered in the calculation as being very small, hence as being negligible with respect to the diameter of the disk.

The general principle of such calculation can be used whatever the geometrical shapes of the satellite particles and of the core particles.

Also, the calculations which are made will allow for the differences in the size of the particles, using for example, mean sizes or mean masses for said particles.

Accordingly, in a preferred embodiment, the percentage by weight of the satellite particles expressed in relation to the total dry material is preferably close or equal to the theoretical percentage given by the formula:

$$C = \frac{S_o \rho V}{S_o \rho V + \rho_o V_o S} \times 100$$

in which S, $S_o$, $\rho$, $\rho_o$, V and $V_o$ have the meanings indicated in Table I hereafter.

According to a particular embodiment, said dispersing liquid contains a binding compound designed to help the satellite particles to adhere to the core particles.

Advantageously, said binding compound is dissolved in the dispersing liquid which serves as a vector.

According to another variant, the binding compound can be just placed in suspension in the dispersing liquid serving as vector.

Examples of suitable binding compounds are carboxymethylcellulose, hydroxypropylmethylcellulose, methylcellulose, polyvinylpyrrolidone, ethylcellulose, hydroxypropylcellulose or polymethacrylates.

The binding compound can also be added with plasticizers or antiadhesive agents to prevent the agglomeration of particles of organized powder.

In another variant of embodiment of the process according to the invention, adhesion is achieved between the satellite particles and the core particles by using a material to produce at least one of the sets of particles which can be softened or melted at the temperature of the gaseous fluid used for evaporating the dispersing liquid.

Also, in this case, the temperature of the gaseous fluid, which is higher than the softening temperature of the satellite particles and/or core particles, is generally sufficiently high for the evaporation of the dispersing liquid to be quick and complete and for the particles reaching the cyclone of the installation to be absolutely dry.

The process according to the invention can, for example, be carried out in a conventional evaporation installation comprising a spraying enclosure, connected, on the one hand, to a vat for dispersion of the core particles and of the satellite particles, and, on the other hand, to a cyclone, such as an atomization installation. The dispersion is introduced under pressure (gas compressed under about 3 to 10 bars, and preferably 7 bars) into the spraying enclosure, for example through the orifice of a nozzle, the droplets thus obtained being dried with a hot gas (for example air at about 150°-250° C.).

The present invention also relates, in a second aspect, to the organized powders thus obtained, as well as to the applications of such organized powders which are well known to anyone skilled in the art and described in

TABLE I

| Satellite/core | $S_o$ | S | $n = \frac{S_o}{S}$ | $M_o = \rho_o V_o$ | $M = \rho V$ | $R = \frac{nM}{M_o}$ |
|---|---|---|---|---|---|---|
| sphere/sphere | $\pi D^2$ | $\pi \frac{d^2}{4}$ | $4 \frac{D^2}{d^2}$ | $\rho_o \pi \frac{D^3}{6}$ | $\rho \pi \frac{d^3}{6}$ | $4 \frac{\rho d}{\rho_o D}$ |
| sphere/disk | $\pi \frac{D^2}{2}$ | $\pi \frac{d^2}{4}$ | $2 \frac{D^2}{d^2}$ | $\rho_o \pi \frac{D^2}{4} h$ | $\rho \pi \frac{d^3}{6}$ | $\frac{4}{3} \frac{\rho}{\rho_o} \frac{d}{h}$ |

$S_o$ = total surface of a core particle
S = portion of surface of core particle occupied by a satellite particle
n = number of satellite particles for one core particle
$M_o$ = mass of a core particle
M = mass of a satellite particle
R = relative portion by weight (or mass) of satellite particles relatively to the core particles
D = diameter of a core particle
d = diameter of a satellite particle
$\rho_o$ = density of core particles
$\rho$ = density of satellite particles
h = height of a core particle (case of a disk)
V = volume of a satellite particle
$V_o$ = volume of a core particle the literature. In particular, said organized powders can be used in the cosmetic, pharmaceutical, phytopathological fields, in the agri-foodstuffs industry, in the fields of pesticides, paints or metallurgy.

By way of examples, the core particles can be constituted by or contain the following products: polyester, polyethylene, polystyrene, polymethylmethacrylate, cellulose, Nylon 6, Nylon 12, Teflon, vinyl chloride or even an epoxy, acrylic or methacrylic resin.

As used herein, the term "Nylon" is a generic term used for any long-chain synthetic polymeric amide which has recurring amide groups as an integral part of the main polymer chain. Although the nylon of the recent invention is utilized in particle form, the composition of said nylon is identical to the various compositions found in nylon fibers in use today. Nylon fibers, as defined by the U.S. Federal Trade Commission, are made from a manufactured substance which is any long chain synthetic polyamide having recurring amide groups (NH—CO—) as an integral part of the polymer chain; and include those nylon fibers derived from the polyamide condensation product of hexamethylenediamine and adipic acid (i.e. Nylon 6,6), as well as those derived from the polycondensation of epsilon caprolactam (i.e. Nylon 6).

Similarly, the satellite particles can be constituted by or contain the following products: a mineral powder such as for example talc, kaolin, mica, vermiculite, silica; an organic powder such as for example a Nylon or polyethylene powder; a mineral pigment such as for example titanium oxide, zinc oxide, iron oxide, iron titanate, carbon black, manganese purple, chromium oxide, cobalt blue, Prussian blue.

Advantageously, the core particles and the satellite particles are selected from the following couples of sets of particles: Nylon-titanium oxide, Nylon-silica, Nylon-yellow iron oxide, Nylon-cobalt blue, polystyrene-titanium oxide, polyethylene-titanium oxide, polyethylene-yellow iron oxide, polyethylene-black iron oxide, polyethylene-cobalt blue.

Besides the economical advantage, already mentioned, over the known processes, the process according to the invention offers many other advantages. For example, it affords the possibility of obtaining a very uniform covering of the core particles whatever their shape, including the strip shapes. It also affords the possibility of very readily producing organized powders constituted of satellite particles and core particles of comparable strength, using a binder if necessary.

Other objects, characteristics and advantages of the invention will also emerge from the following explanatory description with reference to the examples of embodiment of the invention, which examples are given merely by way of illustration, and which therefore cannot in any way limit the scope of the invention.

EXAMPLE 1

93 g of Nylon 12 powder (substantially spherical- or ball-shaped particles) with particles of mean diameter equal to about 5 $\mu$m and of density about 1.02 g/cm3 are used as core particles, and 7 g of titanium dioxide (substantially spherical particles) with particles of mean diameter of about 0.02 $\mu$m and of density about 4 g/cm3 are used as satellite particles.

Said two groups of core particles and satellite particles are placed homogeneously in suspension in an aqueous solution containing 899 g of water and 1 g of TWEEN 20.

The suspension is then sprayed inside an atomizer, in a gaseous fluid constituted by air heated to a temperature of about 230° C., under a pressure of 7 bars for a liquid flowrate of 5 liters per hour.

An organized powder is thus obtained in which the core particles comprise on their surface a plurality of satellite particles. Due to the relative proportion used in the present case, the satellite particles constitute a uniform covering over the surface of the core particles.

Using the experimental protocol described in Example 1, a certain number of organized powders has been produced with different types of materials being used for the core particles and for the satellite particles, and particularly, by varying the relative proportions by weight of the core particles relatively to the satellite particles.

The results from these tests are given in Table II and show that the quality of the obtained covering varies from average to excellent, depending on the experimental conditions selected.

In the latter case, the covering obtained is total and regular.

TABLE II

| | Composition | | | Dispersing liquid (solvent) | P percentage of dry material | Vector gas | Temperature °C. | Covering quality result |
| --- | --- | --- | --- | --- | --- | --- | --- | --- |
| | Nature | Form/$\phi$ | Quantity by weight (1) | | | | | |
| Core particle | Nylon 12 SP 500 | balls 5$\mu$ | 90% | H$_2$O | 10% | air | 200–230 | *** |
| Satellite particle | TiO$_2$ (P25) | balls 0.02$\mu$ | 10% | | | | | |
| Core particle | Nylon 12 SP 500 | balls 5$\mu$ | 95% | H$_2$O | 10% | air | 150–200 | *** |
| Satellite particle | SiO$_2$ (Aerosil 200) | balls 0.012$\mu$ | 5% | | | | | |
| Core particle | Polystyrene | balls 6$\mu$ | 85% | H$_2$O | 10% | air | 150–200 | ** |
| Satellite particle | TiO$_2$ | balls 0.02$\mu$ | 15% | | | | | |
| Core particle | Nylon 12 Flakes | disks 10$\mu$ | 90% | H$_2$O | 10% | air | 150–200 | ** |
| Satellite particle | SiO$_2$ (Aerosil 200) | balls 0.012$\mu$ | 10% | | | | | |
| Core particle | Nylon 12 (Flakes) | disks 12$\mu$ | 70% | H$_2$O | 10% | air | 180–230 | ** |
| Satellite particle | TiO$_2$ | balls 0.02$\mu$ | 30% | | | | | |
| Core particle | Polyethylene | ball2 10$\mu$ | 70% | H$_2$O | 10% | air | 120–150 | * |
| Satellite particle | TiO$_2$ | balls 0.02$\mu$ | 30% | | | | | |
| Core particle | Nylon 12 Flakes | balls 12$\mu$ | 70% | H$_2$O | 10% | air | 150–180 | ** |
| Satellite particle | yellow iron oxide | pins 0.5$\mu$ | 30% | | | | | |
| Core particle | Nylon 12 (SP 500) | balls 5$\mu$ | 70% | H$_2$O | 10% | air | 150–190 | ** |
| Satellite particle | yellow iron oxide | pins 0.5$\mu$ | 30% | | | | | |
| Core particle | polyethylene | balls 10$\mu$ | 70% | H$_2$O | 10% | air | 130–150 | * |

TABLE II-continued

| | Composition | | | Dispersing | P | | | Covering |
| | Nature | Form/φ | Quantity by weight (1) | liquid (solvent) | percentage of dry material | Vector gas | Temperature °C. | quality result |
|---|---|---|---|---|---|---|---|---|
| Satellite particle | black iron oxide | balls 0.2μ | 30% | | | | | |

$R = \dfrac{\text{Quantity by weight of satellite particles}}{\text{Quantity by weight of core particles}}$ $P = \dfrac{\text{Quantity by weight of satellite particles + core particles}}{\text{Quantity by weight of dispersing liquid}}$ (1) The indicated quantities are proportions by weight with respect to the dry material.
*average
**good
***excellent

EXAMPLE 2

The same experimental protocol as in Example 1 is used, except that a certain quantity of a binder is introduced in the aqueous dispersing solution.

The results obtained are given in Table III in a similar presentation to Table II.

This embodiment makes it possible, in particular, to overcome the disadvantages of the known processes, in those cases where the satellite particles find difficulty in settling on the core particles.

Obviously, the invention covers all the means which constitute technical equivalents of the described means as well as the various combinations thereof.

said dispersing liquid, said satellite particles adhering to said core particles to form said organized powders.

2. The process of claim 1, wherein the organic polymer of the core particles is selected from the group consisting of polyester, polyethylene, polystyrene, polymethylmethacrylate, cellulose, a polyamide, polytetrafluorethylene, vinyl chloride, an epoxy resin, an acrylic resin, and a methacrylic resin.

3. The process of claim 1, wherein the satellite particle is selected from the group consisting of talc, kaolin, mica, vermiculite and silica.

4. The process of claim 1, wherein the satellite particles are selected from the group consisting of a polyamide and polyethylene.

TABLE III

| | Composition | | | | Dispersing | P | | | Covering |
| | Nature | Form/φ | Quantity by weight | Q (2) | liquid (solvent) | percentage of dry material | Vector gas | Temperature °C. | quality result |
|---|---|---|---|---|---|---|---|---|---|
| Core particle | polyethylene | balls 8μ | 60% | | H₂O | 10% | air | 120–150 | ** |
| Satellite particle | cobalt blue | 0.3–0.8μ | 40% | | | | | | |
| Binder | H.P.M.C | | | 0,05% | | | | | |
| Core particle | Nylon 12 | disks 10μ | 70% | | H₂O | 10% | air | 150–190 | * |
| Satellite particle | cobalt blue | 0.3–0.8μ | 30% | | | | | | |
| Binder | C.M.C | | | 0,05% | | | | | |
| Core particle | Nylon 12 (SP 500) | balls 5μ | 70% | | H₂O | 10% | air | 150–200 | * |
| Satellite particle | cobalt blue | 0.3–0.8μ | 30% | | | | | | |
| Binder | H.P.M.C | | | 0,05% | | | | | |
| Core particle | polyethylene | disks 20μ | 75% | | H₂O | 10% | air | 120–150 | ** |
| Satellite particle | cobalt blue | 0.3–0.8μ | 25% | | | | | | |
| Binder | H.P.M.C | | | 0,05% | | | | | |

Q = Percentage of binder in the aqueous solution
C.M.C = Carboxymethylcellulose
H.P.M.C = Hydroxypropylmethylcellulose
* average
** good
*** excellent

We claim:

1. A process for producing organized powders suitable for use in cosmetic pharmaceutical or phytopathological applications, said organized powders obtained from particles of different sizes belonging to at least two sets of particles, each said set being of substantially homogeneous sizes, and comprising respectively, at least one set of core particles consisting of an organic polymer and at least one set of satellite particles smaller in size than said core particles, said satellite particles forming a substantially uniform monolayer enveloping the surface of each of said core particles, said process for forming said organized powders consisting essentially of preparing a homogeneous dispersion of each said set of particles in a dispersing liquid at a ratio of said satellite particles to said core particles appropriate to form said monolayer of said satellite particles onto said core particles, then spraying said homogeneous dispersion containing said satellite particles and said core particles at a temperature sufficient to evaporate said dispersing liquid, said satellite particles adhering to said core particles to form said organized powders.

5. The process of claim 1, wherein said satellite particles comprise a pigment.

6. The process of claim 5, wherein said pigment is selected from the group consisting of titanium oxide, zinc oxide, iron oxide, iron titanate, carbon black, manganese purple, chromium oxide, cobalt blue, Prussian blue.

7. The process of claim 1, wherein the spraying of said homogeneous dispersion is performed in a gaseous fluid brought to a temperature causing evaporation of the dispersing liquid.

8. Process according to claim 1, characterized in that the spraying of said homogeneous dispersion is performed inside an enclosure under conditions of pressure and temperature to obtain said organized powder.

9. Process according to claim 7, characterized in that the homogeneous dispersion is produced with only one liquid.

10. Process according to claim 9, characterized in that the dispersing liquid is constituted by water or an aqueous solution.

11. Process according to claim 7, characterized in that the gaseous fluid is constituted by air.

12. Process according to claim 1, further characterized in that the satellite particles have a mean diameter and the core particles have a mean diameter, the mean diameter of the satellite particles is less than or equal to about one fifth of the mean diameter of the core particles.

13. Process according to claim 7, further comprising, prior to the introduction of the particles, the addition to the dispersing liquid, of an efficient quantity of wetting substance.

14. Process according to claim 7, further characterized in that the percentage by weight of the satellite particles expressed with respect to the total dry material is close or equal to the theoretical percentage given by the formula:

$$C = \frac{S_o \rho V}{S_o \rho V + \rho_o V_o S} \times 100$$

in which S is the portion of surface of core particle occupied by a satellite particle, $S_o$ is the total surface of a core particle, is the density of the satellite particles, $_o$ is the density of $\rho$, the core particles, V is the volume of a satellite particle and $V_o$ is the volume of a core particle $\rho_o$.

15. Process according to claim 14, further characterized in that said dispersing liquid contains at least one binding compound designed to help the satellite particles to adhere to the core particles.

16. Process according to claim 15, characterized in that the binding compound is dissolved in the dispersing liquid.

17. Process according to claim 15, characterized in that the binding compound is constituted by carboxymethylcellulose or by hydroxypropylmethylcellulose.

18. Process according to claim 10, further characterized in that the particles selected from the group consisting of the satellite particles, the core particles and both satellite particles and the core particles are constituted of which can be softened or melted at the temperature of the gaseous fluid used for evaporating the dispersing liquid.

19. Process according to claim 18, further characterized in that the core particles and the satellite particles are selected from and, the group consisting of the following couples of sets of particles: Nylon-titanium oxide, Nylon-silica, Nylon-yellow iron oxide, Nylon-cobalt blue, polystyrene-titanium oxide, polyethylene-yellow iron oxide, polyethylene-black iron oxide, polyethylene-cobalt blue.

* * * * *

UNITED STATES PATENT AND TRADEMARK OFFICE
CERTIFICATE OF CORRECTION

PATENT NO. : 5,374,452
DATED : December 20, 1994
INVENTOR(S) : Alain Meybeck and Philippe Antoine It is certified that error appears in the above-indentified patent and that said Letters Patent is hereby corrected as shown below:

On the title page, item [76], the second inventor, PHILIPPE ANTOINE, insert a comma after "8", delete "Gén/e,acu/e/ral" and insert --Général--.

Item [76]: Assignee of record was omitted on the first page of the patent. Please insert the Assignee as follows:

LVMH RECHERCHE

Signed and Sealed this

Twenty-seventh Day of February, 1996

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,374,452
DATED : December 20, 1994
INVENTOR(S) : Alain Meybeck and Philippe Antoine It is certified that error appears in the above-indentified patent and that said Letters Patent is hereby corrected as shown below:

On the title page, item [76], the second inventor, PHILIPPE ANTOINE, insert a comma after "8", delete "Gén/e,acu/e/ral" and insert --General--.

Item [73]: Assignee of record was omitted on the first page of the patent. Please insert the Assignee as follows:

LVMH RECHERCHE
Nanterre, FRANCE

This Certificate supersedes Certificate of Correction issued February 27, 1996.

Signed and Sealed this

Eleventh Day of June, 1996

Attest:

BRUCE LEHMAN

*Attesting Officer*     *Commissioner of Patents and Trademarks*